United States Patent [19]

Spengler

[11] Patent Number: 4,528,612

[45] Date of Patent: Jul. 9, 1985

[54] APPARATUS FOR CONDITIONING A SPACE BY GAS IONIZATION

[76] Inventor: Walter Spengler, Strehlgasse 23, CH-4105 Biel-Benken, Switzerland

[21] Appl. No.: 487,198

[22] Filed: Apr. 21, 1983

[30] Foreign Application Priority Data

Apr. 21, 1982 [CH] Switzerland ................. 2409/82

[51] Int. Cl.³ ............................................. H05F 3/06
[52] U.S. Cl. .................................. 361/213; 361/216; 361/231
[58] Field of Search ............... 361/213, 216, 229, 231, 361/214, 215, 220

[56] References Cited

U.S. PATENT DOCUMENTS

| | | | |
|---|---|---|---|
| 1,169,428 | 1/1916 | Rogers | 361/213 |
| 3,292,042 | 12/1966 | Michener et al. | 361/231 X |
| 3,308,343 | 3/1967 | Smith et al. | 361/213 |
| 3,308,344 | 3/1967 | Smith et al. | 361/213 X |
| 4,319,302 | 3/1982 | Moulden | 361/231 |
| 4,366,525 | 12/1982 | Baumgartner | 361/231 |

Primary Examiner—Reinhard J. Eisenzopf
Attorney, Agent, or Firm—Burgess, Ryan & Wayne

[57] ABSTRACT

Apparatus for ionizing air and introducing the ions into a computer room or the like, to condition the air and/or discharge static electricity. The air is introduced from a plenum chamber into a number of bulb-shaped outlets which extend into the space to be conditioned and which have perforated walls through which the air can escape into the space. A pair of ionization electrodes in the center of each outlet ionizes the air immediately before it escapes into the surrounding space.

9 Claims, 4 Drawing Figures

APPARATUS FOR CONDITIONING A SPACE BY GAS IONIZATION

FIELD OF THE INVENTION

The present invention concerns a process for the ionization of a fluid, such as air used for the conditioning of a space or a zone for air-conditioning by ionization or, further, for discharging static electricity and of the type in which the fluid is subjected in an air-conditioning enclosure to the action of at least one ionization agent, such as a set of electrodes, before being discharged into the space to be conditioned by ionization.

BACKGROUND OF THE INVENTION

The ionization devices known per se generally comprise sets of electrodes brought to a relatively high alternating or direct electric current (for example, comprised between 2 and 5 kV for installations of considerable flow of air). These electrodes are disposed along geometric grids in conduits or pipe-lines through-crossed by the gas or air to be ionised and are present in the form of points or wires borne by the walls of these conduits or pipe-lines. These ionization installations give relatively satisfactory results in industrial installations for the treatment of gas by ionization such as dust-removing installations by electrostatic precipitation but prove to be much less efficient in air conditioning installations by ionization.

These reduced-scale ionisation installations are, for example, designed to remove static electricity that appears on textile fibers during trituration or in sensitive electric equipment such as computors or integrated circuits, particularly during their production and their assembly. This lack of efficiency of medium-size ionisation installations seems to be due to the fact that, for reasons of costs and organisation of the air-conditioning installation, ionization electrodes are installed in an enclosure for the treatment of air and the treated air is distributed by relatively long conduits in utilisation zones such as the proximity of covers of textile threads charged with static electricity or, furthermore, assembly tables of printed circuits.

After positive or negative ionization of the air to be treated, the relatively turbulent passage of this ionised air in the distribution conduits provokes a "recombination" of the positive and negative ions, previously disassociated and the "recombination" or depolarization of the air considerably reduces the ionization rate of the treated air when it is delivered into the utilisation zone constituting a space to be air-conditioned by ionisation.

DESCRIPTION OF THE PRIOR ART

In order to reduce the recombination of the ions, it has already been proposed to dispose the ionization agent immediately adjacent to the discharge outlet inside the discharge pipe-line of ionised air but experience shows that the ions recombine during passage through the discharge vanes or protection devices that it is necessary to dispose about the electrodes constituting the ionization organ.

According to another embodiment known per se, the ionization of the air is carried out by using radiation emitter bodies that can be fixed on to the blades of a free air blowing screw. The risks of recombination during the discharge of the air are thus radically reduced but such an apparatus cannot be applied for use in jet blowing or central blowing means installations.

SUMMARY OF THE INVENTION

The present invention has for object to almost completely remove the drawback of the recombination of the ions of the fluid such as air treated by an ionisation operation, without considerably increasing the cost of the apparatus of treatment by ionisation and by using a central blowing installation.

With this purpose, the ionization process of a fluid such as air used for the conditioning of a space or a zone to be air-conditioned by ionisation or, further, to discharge the static electricity and of the type in which the fluid is subjected in an air-conditioning enclosure to the action of at least one ionization agent such as a set of electrodes before being discharged into the space to be air conditioned by ionization, in which an ionisation organ is disposed immediately adjacent to each of the discharge outputs of the air-conditioning enclosure in the space to be air-conditioned in order to reduce the possibilities of recombination and/or depolarization of the ions generated by the ionisation agent prior to their discharge in the space to be air-conditioned, according to the invention, is a process wherein the ionization organ is disposed adjacent to the output but in the space to be air-conditioned outside each of the discharge pipe-lines of the air-conditioning enclosure.

According to the process of the invention, it is necessary to dispose at least one set of ionization electrodes which thus increases the cost but again a single installation generating high ionization voltage can be used and the cost of the entire ionization installation is, in most cases, only slightly increased whereas the efficiency of the installation is considerably improved.

According to another embodiment of the invention, the ionization organ is arranged outside the discharge pipe-line of the air-conditioning enclosure but separated from the space to be air-conditioned by walls of a distribution chamber perforated by a plurality of passages from which the fluid is discharged into the space to be air-conditioned by a plurality of outlets like those of a rose of a watering-can and the ionization agent is, preferably, positioned substantially in the center of the distribution chamber.

According to one improvement of this latter process, the perforated walls of the distribution chamber are arranged so as to form protection with respect to the ionization agent if said agent presents exploitation dangers such as electrical dangers for the electrodes or irradiation dangers for a radio-active source.

Means for reducing the turbulence can be disposed in the air-conditioning enclosure immediately adjacent to each ionisation organ. These turbulence-reduction means are preferably placed up stream from each ionization agent in the direction of the flow of the fluid to be air-conditioned.

In the device for operating the process according to the invention, the discharge of the air-conditioning enclosure is carried out by a plurality of discharge sections adjacent to each of the outputs of which is disposed at least one ionization agent in order to reduce the possibilities of recombination and/or depolarization of the ions generated by the ionisation organ. According to the invention the ionization agent is placed adjacent to the outlet but in the space to be air-conditioned outside each of the discharge pipe-lines of the air-conditioning enclosure.

According to another embodiment of the invention, the ionization agent is separated from the space to be air-conditioned by walls, perforated by a plurality of passages, of a distribution chamber from which the fluid is discharged into the space to be air-conditioned by a plurality of outlets like those of a rose of a watering-can. The ionization agent is thus disposed, preferably, substantially in the centre of the distribution chamber and, as a variant, the perforated walls of the distribution chamber are provided so as to form protection with respect to the invention ionization agent if said agent presents dangers of exploitation, such as electrical dangers for the electrodes or irradiation dangers for a radio-active source.

According to a further embodiment of the invention, when the means for reducing the turbulence are disposed in the air-conditioning enclosure adjacent to the ionization organ, these turbulence-reducing means are positioned immediately downstream from the air-conditioning agent in the direction of the flow of the fluid.

The turbulence-reducing means can be constituted by electrodes of the ionization agent, these electrodes being arranged in the form of blades or threads.

As a variant, turbulence-reducing means are provided a flattened form of the discharge section of the air-conditioning enclosure in order to direct the air flow in the form of a relatively thin blade prior to its passage before the ionization agent. Furthermore, the discharge pipe-line(s) of the air-conditioning enclosure can have a form converging in the direction of the ionization agent in such a way as to center exactly on the ionization organ, such as at least one electrode, the air jet to be ionized or deionized.

BRIEF DESCRIPTION OF THE DRAWINGS

Other aims, advantages and characteristics of the invention will become evident by reading through the description of various embodiments of the invention, given by way of non-limitative illustration and with respect to the annexed drawing in which.

DESCRIPTION OF THE PREFERRED EMBODIMENTS

Figure 1:
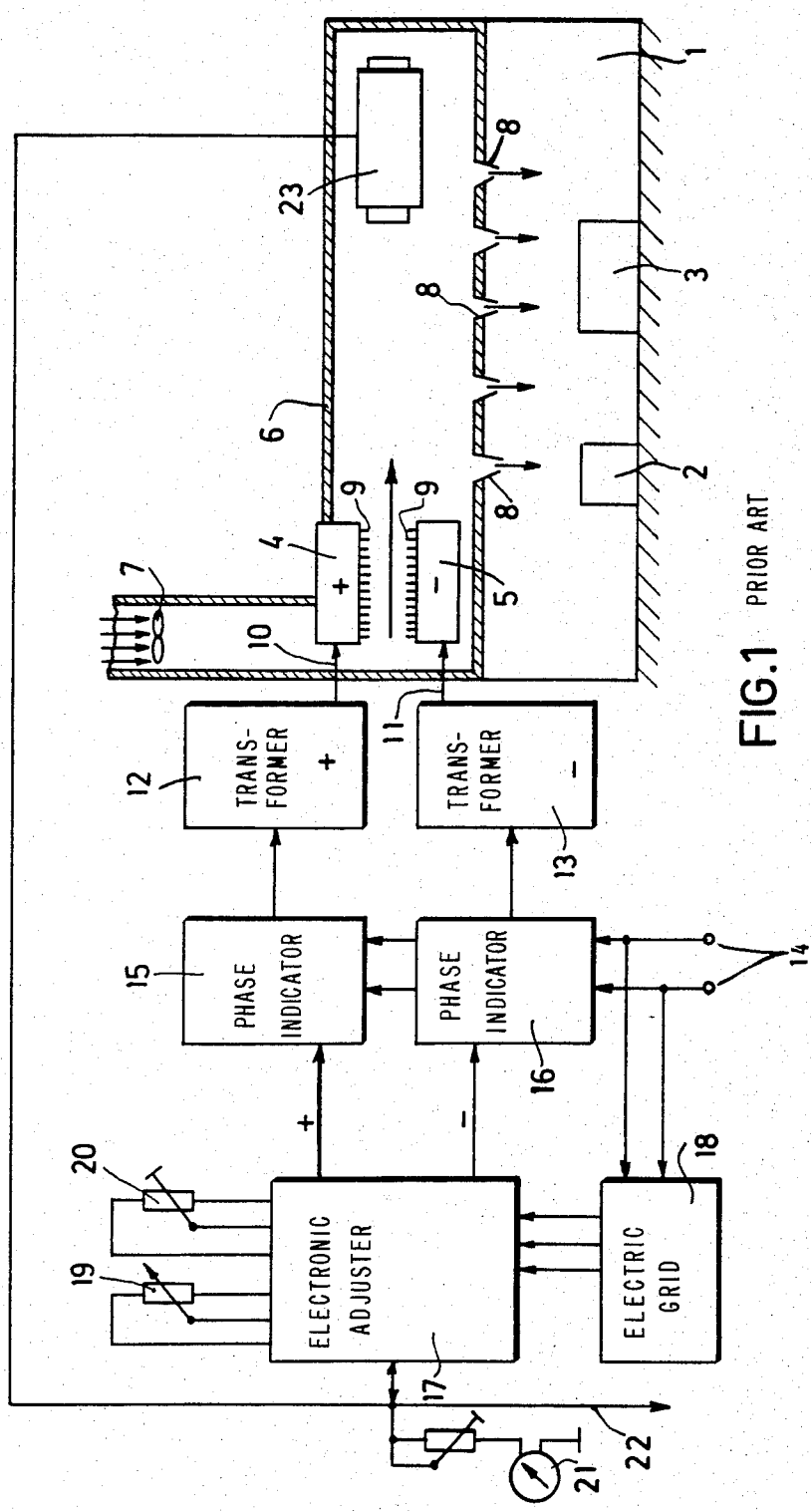
FIG. 1 is a schematic representation of an ionization installation according to the state of the art with a synoptic diagram of the electrocal equipment part.

The air ionization installation known per se, and represented in FIG. 1, aims at increasing the content of the discharged air into air-conditioning site 1 in negative or positive ions according to requirements of the electrostatic discharge of machines or apparatus 2, 3, disposed in this site. In order to do this, positive 4 and negative 5 electrodes are arranged in an air pipe-line 6 in which the previously filtered external air is blown by ventilation 7 and delivered into site 1 by a plurality of outlet mouths or openings 8. In order to increase their electric efficiency electrodes 4 and 5 produced in the form of one or several sheets, are equipped with points 9 which constitute concentration zones of the gradient of the electric potential in the air to be treated and from which are formed ions that are scattered in the air to be distributed by openings 8.

Electrodes 4 and 5 are connected through the intermediary of cables 10 and, respectively, 11, to transformers 12 and 13 generating alternating or direct high voltage (in the latter case, rectifiers, not shown, are intercalated). Transformers 12 and 13 are connected to phases 14 of an electric grid by the intermediary of phase indicators 15 and 16 controled by an electronic adjuster 17 connected to the electric grid in 18 and subjected to an adjustment of the instructions value 19 via an amplifier 20. The electronic adjuster 17 is connected to an electric field indicator 21, itself connected, where necessary, to an electric field recorder by a wiring 22. An ionisation indicator 23 placed in pipe-line 6 can supply a negative feed-back indication to the electronic adjuster 17 that monitors, according to requirements, the voltage and the direction of the voltage of the adjustment electrodes 4 and 5.

Figure 2:
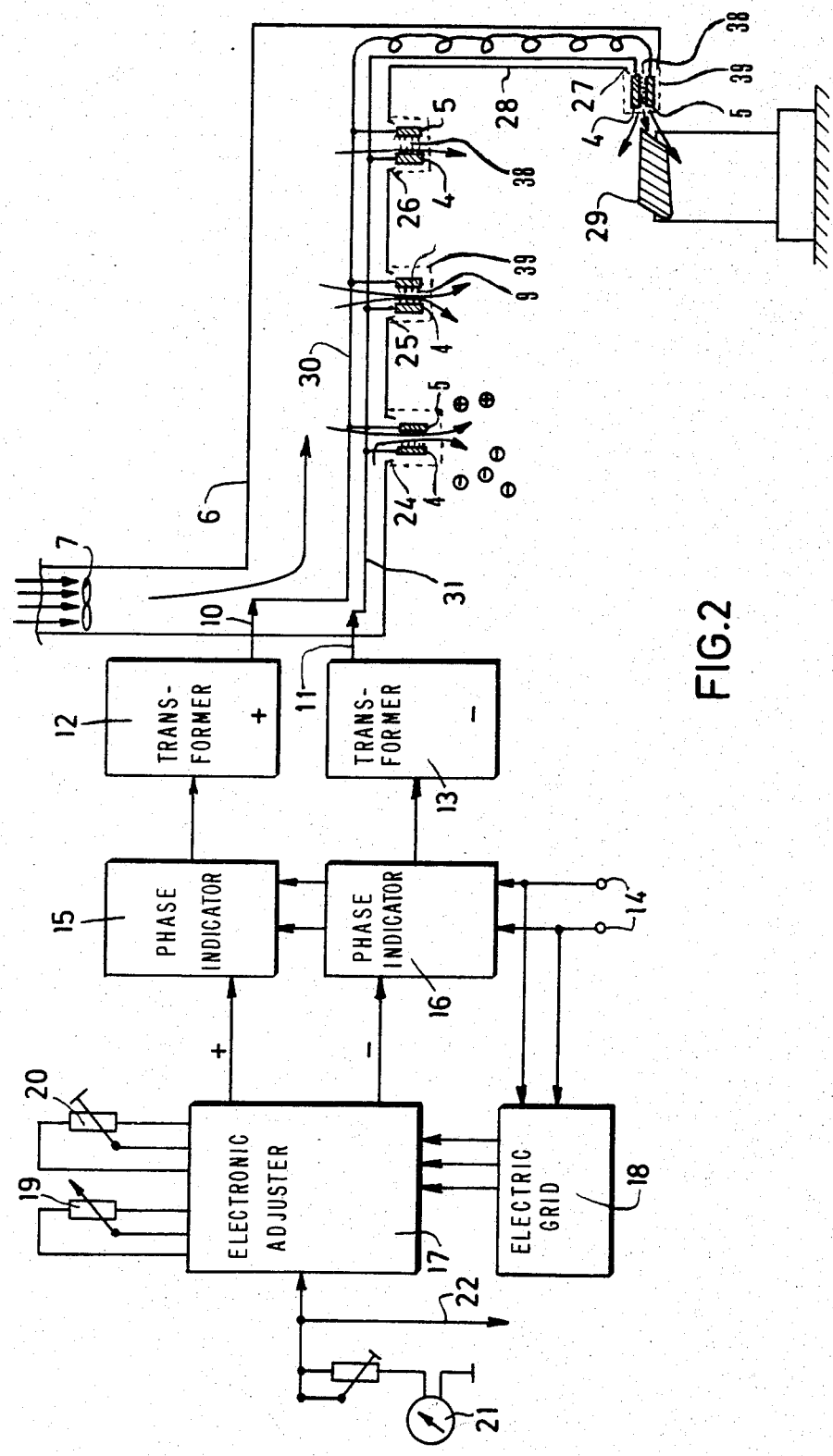
FIG. 2 represents a modified version according to the invention of the installation of FIG. 1.

If reference is made to the embodiment of the invention shown in FIG. 2, in which the elements identical to those of FIG. 1 have the same references, it can be seen that positive 4 and negative 5 electrodes that were disposed in a single zone of pipe-line 6 considerably downstream of outlet openings 8 of air, are brought right to the outlet of each of slightly converging discharge outlets 24, 25, 26, 27 of pipe-line 6 outside this pipe-line and already in the site to be air-conditioned. In order to do this, high voltage cables 10 and 11 are extended to the inside or the outside of pipe-line 6 and are connected to plates of electrodes 4, respectively 5, provided where necessary, with points 9 and generally having smaller dimensions than electrodes plates 4 and 5 of the example of FIG. 1.

Pipe-line 6 can be extended by conduit 28 having a smaller diameter, feeding output 27 in order to serve, for example, a static electricity discharge workplace of a sheet of textile threads 29. The number of electrodes is multiplied by the number of discharge outlets that it is obviously of interest to reduce in the example of the invention, but the actuation and generation equipment of ionization high voltage remains identical to that of FIG. 1 according to the state of the art. As can be easily imagined in considering FIG. 2, the possibilities of "recombination" of positive and negative ions in conduit 6 under the effect of turbulence and shocks against the walls of this conduit are radically eliminated and the yield of the ionisation treatment is considerably increased in such a ratio that it largely compensates the increase of the number of electrodes and the necessity of setting the high voltage cables or insulated conductors 30 and 31 from output cables 10 and 11 of the high voltage generating equipment.

In solutions known per se, the electrodes are recessed inside a short connecting tube at a discharge outlet and this arrangement presents the advantage of protecting the electrodes from risks of accidental short circuiting. According to the invention, it is wished to reduce the risks of recombination of the ions and to facilitate their rapid diffusion in the ambiance to be air conditioned. For this, it is possible to place electrodes 4 and 5, for example in the form of sheets of threads, right at the discharge outlets connecting tubes of the feed pipe-lines to constituting an air-conditioning enclosure. FIG. 2 shows one solution in which electrodes 4 and 5 are placed in the space to be air-conditioned right at the outlet of exit pipe-lines 24–27 in converging form in such a way that the intercalated space 38 between points 9 is blown through by the air jet that escapes from outputs, to be diluted in the atmosphere of the space to be air-conditioned. When electrodes 4, 5 present dangers of short circuiting or electrocution, it is possible to surround them by a protection wall or cage or screen 39 perforated by a multitude of passages. The ionization indicator 23 supplying a feed back to the electronic adjuster 17 is either removed, or placed adjacent to a discharge output beyond electrodes 4, 5.

Figure 3:
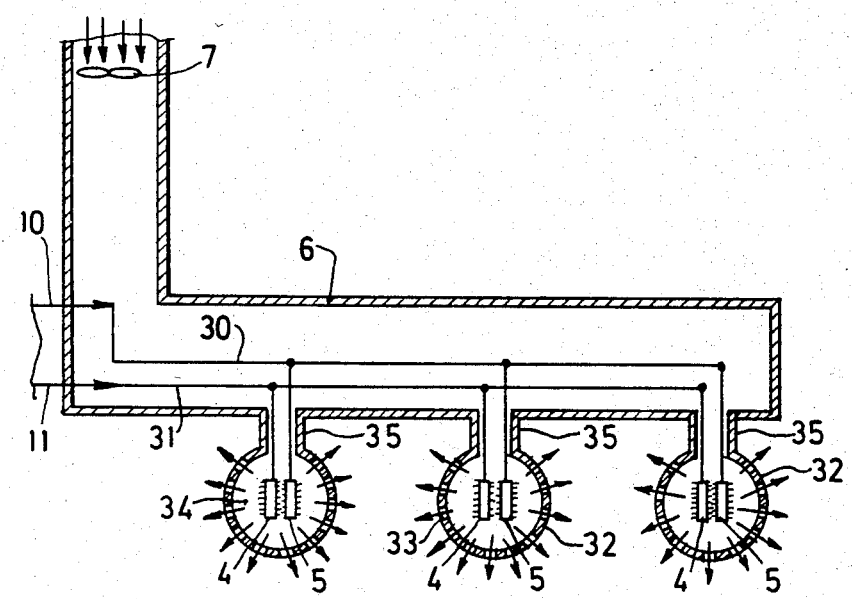
FIG. 3 represents in a diagrammatic section an embodiment of the invention applicable to a distribution of existing ionised air provided with a rain type distribution system.

In the embodiment shown in FIG. 3, only the arrangement of the ionization electrodes 4 and 5 with respect to the pipe-lines and distribution conduit of air or flow in general is shown. It has been supposed that it concerns an air distribution of the rain type from distribution heads in the form of a rose of a watering-can 32 connected to pipe-line 6 in order to distribute air in all directions by a multitude of small holes 33 bored in their wall.

In order to equip such an air distribution installation with an air ionization system according to the invention, it is not possible, of course, to equip each output hole of a set of external ionisation electrodes. Ionization electrodes 4 and 5 connected to high voltage cables 10 and respectively 11 of the generating and monitoring high voltage installation via a set of bars 30 and 31, are disposed substantially in the center of the distribution chamber 34 disposed at the inside of each rose of a watering-can 32 downstream of the delivery conduit 35 to this rose 32, this conduit 35 constituting, in fact, a discharge pipe of the air-conditioning enclosure 6. The possibilities of recombination of the ions are reduced with respect to the state of the art represented in FIG. 1, since it is possible to produce the rose 32 in a material such as plastic material, which only provokes very few "recombinations".

Figure 4:
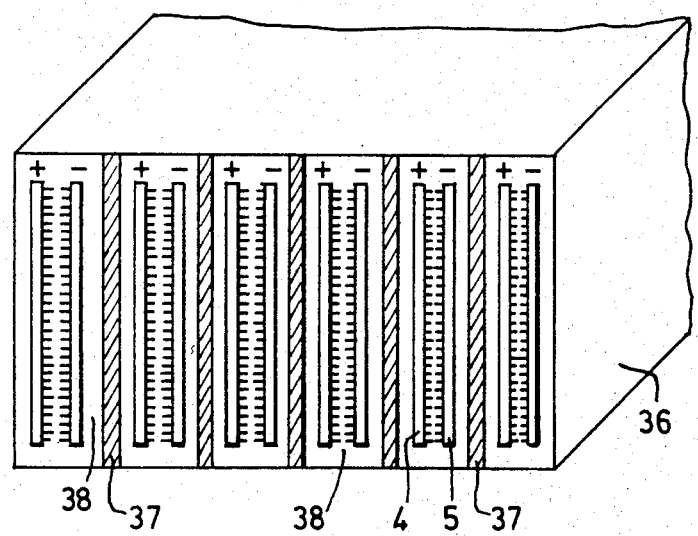
FIG. 4 represents schematically an application of the invention to an ionization installation having a considerable air outflow blown on a reduced section.

The embodiment shown in FIG. 4 applies to a distribution of ionized air of a large section of which only the distribution box 36 is represented in perspective.

According to the invention, box 36 is divided by walls 37 into a plurality of outputs 38 having a flattened section and a set of ionization electrodes 4 and 5 is disposed opposite each of these flat outputs 38. Due to the flattened form of the output sections 38, the air turbulence is reduced and the possibilities of "recombination" and depolarization of the ions produced by electrodes 4 and 5 are reduced after the output of box 36 that ensures a large outflow of the air discharge.

In order to reduce the turubulence in the embodiments of FIGS. 2 and 3, plates or filters in pipe-line 6 are placed immediately upstream from ionization electrodes 4 and 5. Another means of reducing the air turbulence consists of shaping electrodes 4 and 5 in the form of blades disposed in the direction of air flow opposite the pipe-line 6 exists constituting an air conditioning enclosure.

It is understood that the ionisation agent constituted by electrodes 4 and 5 can be replaced by electric charges obtained by friction on an insulating body or by a radioactive body that can carry out at the same time a sterilization function of the fluid discharged by the outputs.

I claim:

1. Apparatus for conditioning a space by ionizing a gas and introducing the ions produced into said space, said apparatus comprising:
   a plenum chamber containing said gas;
   a plurality of outlet ports communicating with said plenum chamber, each of said outlet ports being adapted to be disposed adjacent a space to be conditioned;
   a corresponding plurality of distribution cells, each distribution cell communicating with a corresponding one of said outlet ports and being adapted to be disposed within said space,
   each distribution cell containing ionization means for ionizing said gas,
   each distribution cell having a wall perforated by a plurality of discharge passages through which gas ionized by said ionization means may escape into said space in a corresponding plurality of streams oriented like those of a rose of a watering-can.

2. The apparatus according to claim 1, wherein each of said distribution cell walls comprises a material which has little tendency to cause recombination of ions of said gas.

3. The apparatus according to claim 1, wherein each of said distribution cell walls comprises a plastic material.

4. The apparatus according to claim 1, wherein each of said distribution cells is generally bulb-shaped.

5. The apparatus according to claim 1, wherein each of said ionization means is disposed substantially in the center of the corresponding cell.

6. The apparatus according to claim 1, further comprising turbulence-reducing means disposed in said plenum chamber immediately upstream of said ionization means.

7. The apparatus according to claim 6, wherein said turbulence-reducing means comprises an elongated flattened portion of said plenum for causing said gas to flow toward said outlet ports in the form of a relatively thin blade.

8. The apparatus according to claim 1, wherein each of said discharge passages has a form converging in the direction of the corresponding ionization means.

9. Apparatus for conditioning a space by ionizing a gas and introducing the ions produced into said space, said apparatus comprising:
   a plenum chamber containing said gas;
   a plurality of outlet ports communicating with said plenum chamber, each of said outlet ports being adapted to be disposed adjacent a space to be conditioned;
   a corresponding plurality of generally bulb-shaped distribution cells, each distribution cell communicating with a corresponding one of said outlet ports and being adapted to be disposed within said space,
   each distribution cell containing ionization means for ionizing said gas, each of said ionization means being disposed substantially in the center of the ccorresponding cell,
   each distribution cell having a plastic wall perforated by a plurality of discharge passages through which gas ionized by said ionization means may escape into said space in a corresponding plurality of streams oriented like those of a rose of a watering-can,
   each of said discharge passages having a form converging in the direction of the corresponding ionization means.

* * * * *